(12) United States Patent
Kogan et al.

(10) Patent No.: US 10,359,376 B2
(45) Date of Patent: Jul. 23, 2019

(54) SAMPLE HOLDER FOR X-RAY ANALYSIS

(71) Applicant: Malvern Panalytical B.V., Almelo (NL)

(72) Inventors: Vladimir Kogan, Almelo (NL); Detlef Beckers, Almelo (NL)

(73) Assignee: MALVERN PANALYTICAL B.V., Almelo (NL)

( * ) Notice: Subject to any disclaimer, the term of this patent is extended or adjusted under 35 U.S.C. 154(b) by 205 days.

(21) Appl. No.: 15/214,575

(22) Filed: Jul. 20, 2016

(65) Prior Publication Data

US 2018/0024081 A1 Jan. 25, 2018

(51) Int. Cl.
| | |
|---|---|
| *G01N 23/20* | (2018.01) |
| *G01N 23/20008* | (2018.01) |
| *G01N 23/20025* | (2018.01) |
| *G01N 23/20033* | (2018.01) |
| *G01N 23/20066* | (2018.01) |
| *G01N 23/201* | (2018.01) |
| *G01N 23/22* | (2018.01) |
| *G01N 23/223* | (2006.01) |

(52) U.S. Cl.
CPC ....... *G01N 23/20033* (2013.01); *G01N 23/20* (2013.01); *G01N 23/201* (2013.01); *G01N 23/20008* (2013.01); *G01N 23/20025* (2013.01); *G01N 23/20066* (2013.01); *G01N 23/22* (2013.01); *G01N 23/223* (2013.01); *G01N 2223/054* (2013.01)

(58) Field of Classification Search
CPC ............. G01N 23/20; G01N 23/20008; G01N 23/20025; G01N 23/20033; G01N 23/20066; G01N 23/201; G01N 23/223

USPC ....... 378/71, 73, 79, 80, 208, 44–46, 86, 88, 378/90
See application file for complete search history.

(56) References Cited

U.S. PATENT DOCUMENTS

| | | | | |
|---|---|---|---|---|
| 3,646,318 A * | 2/1972 | Melin | ..... | G05D 23/22 219/209 |
| 6,041,095 A * | 3/2000 | Yokhin | ..... | G01N 23/223 378/124 |
| 6,355,217 B1 * | 3/2002 | Kiefersauer | ..... | B01L 3/508 422/547 |
| 6,937,695 B2 * | 8/2005 | Hoshino | ..... | G01N 23/201 250/281 |
| 6,993,113 B2 * | 1/2006 | Hoshino | ..... | G01N 23/201 378/70 |

(Continued)

FOREIGN PATENT DOCUMENTS

DE      10 2004 029 7      1/2005

OTHER PUBLICATIONS

"Gas Cell Oven, Operating Manual", Thorlabs, Inc., GCH25-75, May 19, 2010.

*Primary Examiner* — Allen C. Ho
(74) *Attorney, Agent, or Firm* — Leason Ellis LLP

(57) ABSTRACT

A sample holder 2 for holding a capillary 40 for X-ray analysis has a first thermal transport member 36 on the base portion 14 on one side of a longitudinal slit 12 and a second thermal transport member 38 on the base portion 16 on the other side. The thermal transport members 36, 38 are compressed between a frame 30 and the base portion 14, 16 in the transverse direction to urge the edges of the first and second thermal transport members together, to hold a capillary 40 longitudinally aligned with the longitudinal slit 12.

18 Claims, 5 Drawing Sheets

(56) References Cited

U.S. PATENT DOCUMENTS

| | | | |
|---|---|---|---|
| 7,400,705 B2 * | 7/2008 | Hoshino | G01N 23/201 378/80 |
| 7,424,093 B2 * | 9/2008 | Fukai | G01N 23/223 378/208 |
| 7,436,926 B2 * | 10/2008 | Matoba | G01N 23/223 378/208 |
| 7,542,547 B2 * | 6/2009 | Kogan | G01N 23/20025 378/71 |
| 8,597,598 B2 | 12/2013 | Claeys et al. | |
| 9,008,273 B2 * | 4/2015 | Hodzic | G01N 23/201 356/301 |
| 9,010,202 B2 * | 4/2015 | Stabacinskiene | G01N 23/20033 250/443.1 |
| 9,057,685 B2 * | 6/2015 | Allen | G01N 23/223 |
| 9,255,898 B2 * | 2/2016 | Coquerel | G01N 23/20033 |
| 9,275,844 B2 * | 3/2016 | Bogan | H01J 49/0431 |
| 9,329,143 B2 * | 5/2016 | Schnablegger | G01N 23/20 |
| 9,360,440 B2 * | 6/2016 | Allen | G01N 23/223 |
| 9,383,326 B2 * | 7/2016 | Beumer | G01N 23/223 |
| 9,459,219 B2 * | 10/2016 | Gautsch | G01N 23/20033 |
| 9,488,605 B2 * | 11/2016 | Feser | G01N 23/2206 |
| 9,513,237 B2 * | 12/2016 | Brescello | G01N 23/20 |
| 9,618,461 B2 * | 4/2017 | Ohara | G01N 23/20008 |
| 9,683,950 B2 * | 6/2017 | Sarrazin | G01N 23/20025 |
| 9,927,336 B2 * | 3/2018 | Meisberger | G01N 1/42 |
| 10,113,980 B2 * | 10/2018 | Chung | G01N 23/20008 |
| 10,175,184 B2 * | 1/2019 | Creighton | G01N 23/223 |

\* cited by examiner

SAMPLE HOLDER FOR X-RAY ANALYSIS

FIELD OF INVENTION

The invention relates to a sample holder for X-ray analysis and a method of making X-ray measurements using a sample holder.

BACKGROUND TO THE INVENTION

When carrying out X-ray analysis, such as X-ray diffraction (XRD) or X-ray fluorescence (XRF) analysis, there is a need to hold the sample in position in an X-ray beam. For some types of sample, existing sample holders do a good job.

One type of sample holder holds the sample in a hollow sample holder which may be a capillary. The hollow sample holder can then be mounted in some form of mounting for introduction into X-ray analysis apparatus. The approach using a capillary can give the advantage that the capillary can be relatively low cost and so a new capillary can be used for each new sample, avoiding the need to completely clean the sample holder. Such an approach can therefore be useful for example where contamination from a previous sample could affect measurements.

Such a sample holder may be of use in particular in small angle X-ray scattering (SAXS) measurements such as those proposed in U.S. Pat. No. 7,542,547.

However, in some cases it is necessary to hold samples at a predetermined temperature for analysis. There is therefore a need for a temperature controlled sample holder.

A sample holder for XRD analytical apparatus using a capillary as a sample holder and having a heater for heating the sample in use is taught by U.S. Pat. No. 8,597,598.

However, the arrangement is complicated and does not allow for mounting inside existing equipment.

There thus remains a need for a sample holder that can be thermally controlled to keep the sample at a required temperature that is straightforward to manufacture and use and preferably which can be mounted inside existing equipment.

SUMMARY OF THE INVENTION

According to a first aspect of the invention, there is provided a sample holder for holding a hollow tube for X-ray analysis apparatus, comprising:
  a base portion having an opening for an X-ray beam;
  a first thermal transport member on the base portion on one lateral side of the opening and a second thermal transport member on the other lateral side of the opening;
  wherein the first and second thermal transport members are deformable to compress the hollow tube laterally to hold the hollow tube such that:
    (i) an X-ray beam can pass through the hollow tube without intersecting any part of the sample holder, and
    (ii) there is thermal contact between the hollow tube and the thermal transport member along the length of the hollow tube and around at least part of the circumference of the hollow tube to conduct heat between the hollow tube and the base portion through the thermal transport member.

The inventor has discovered that a particular problem in obtaining an effective design for providing a tube-based sample holder, especially such a sample holder suitable for use in SAXS measurements, is obtaining effective thermal coupling to the hollow tube for holding the sample. One reason for this is that for high quality SAXS measurements the X-ray beam should not pass through parts of the sample holder except for the hollow tube to avoid signal from those other parts of the sample holder. This makes it difficult to arrive at effective thermal contact.

By using a deformable material as the material of the thermal transport members, the tube may be releasably held, i.e. the tube may be supported only by the thermal transport member without requiring glue, screws or the like. The thermal transport members may be formed of a relatively soft material and/or an elastic material. By causing a lateral force between the thermal transport member and tube, by compressing the thermal transport member on introduction of the sample holder, either by a compression member or by the interaction of the tube itself with the thermal transport member the tube may be removed and replaced—the tube is not fixed with glue or other permanent mounting but instead is held between the deformable thermal transport members. This removability is achieved while still providing good thermal contact along the length of the capillary and also providing contact around a good portion of the circumference of the capillary.

Such an arrangement provides a good thermal contact and good control of temperature compared with arrangements such as U.S. Pat. No. 8,597,598 using a radiant heater, while still allowing the tube to be easily removed and replaced.

The opening may be a longitudinal slit and the hollow sample holder may be accurately aligned with the longitudinal slit without requiring the tube to engage with the base nor requiring parts of the compression member or base part to intersect with X-ray beams passing through the longitudinal slit.

The sample holder may further comprise a compression element for compressing the first and/or second thermal transport members to urge the first and second thermal transport members together to hold the hollow tube.

The compression element may be arranged to compress the thermal transport members between the compression element and the base portion in the transverse direction to urge the edges of the first and second thermal transport members together, to hold the hollow tube in a longitudinal direction in the opening.

The sample holder may further comprise channels in the base portion for passing cooling or heating fluid such as liquid or gas through the base portion.

The compression element may conveniently include a plurality of screws passing at least partially through the frame and through the base portion.

A Peltier cell may be integrated with the base portion to provide well-controlled temperature regulation.

The compression member may comprise a second longitudinal slit aligned with the first longitudinal slit.

The sample holder may further comprise a hollow tube held between the thermal transport members. The hollow tube may be a glass or quartz capillary.

The thermal transport members may be permanently fixed to the base portion.

The thermal transport members may be elastic, for example of thermally conductive plastics or thermally conductive rubber. Alternatively, the thermal transport member may be of carbon (graphite, pyrolytic highly oriented graphite, graphenic carbon or similar) or soft ductile metals such as (pure) aluminium, gallium or indium. Alternatively, the thermal transport members may be in the form of a metal spring.

Another aspect of the invention relates to an X-ray apparatus for small angle X-ray scattering comprising:

a sample holder as described above;

an X-ray source for supplying an X-ray beam through the opening to a sample mounted in the hollow tube; and an X-ray detector arranged to detect X-rays scattered by a sample in the sample holder.

The X-rays may be scattered by a small angle, such as less than 10° or preferably less than 8° or 5° to carry out small-angle X-ray scattering (SAXS). Alternatively, the sample may scatter the X-rays by a greater amount, for wide angle X-ray scattering (WAXS).

BRIEF DESCRIPTION OF THE DRAWINGS

Embodiments of the invention will now be described with reference to the accompanying diagrams, in which.

The Figures are schematic and not to scale. Note that section lines are omitted from FIGS. 2 to 6 for greater clarity.

DETAILED DESCRIPTION

Figure 1:
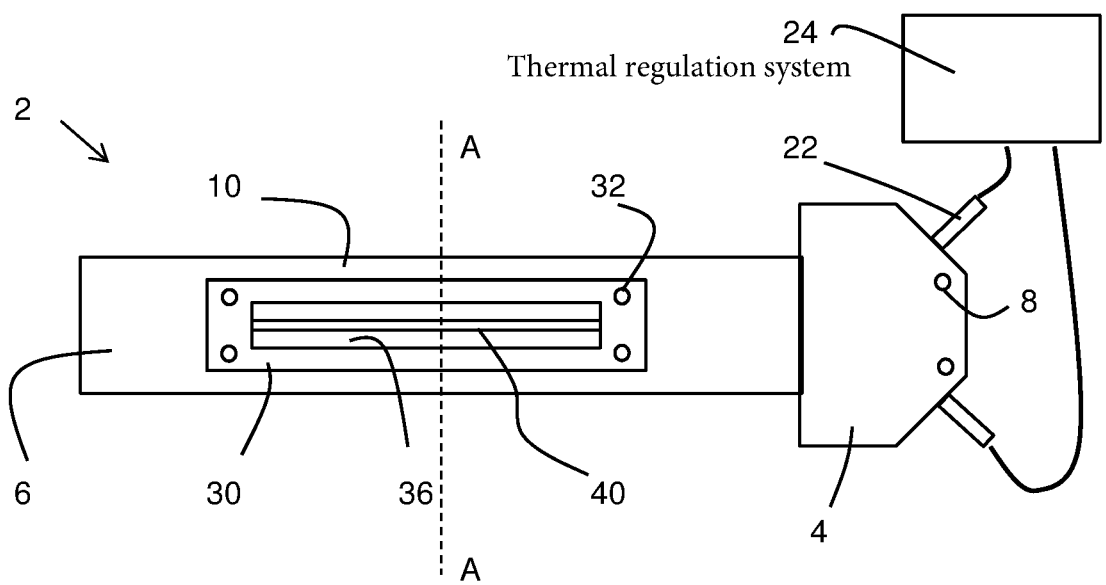
FIG. 1 is a top view of a sample holder.
Figure 2:
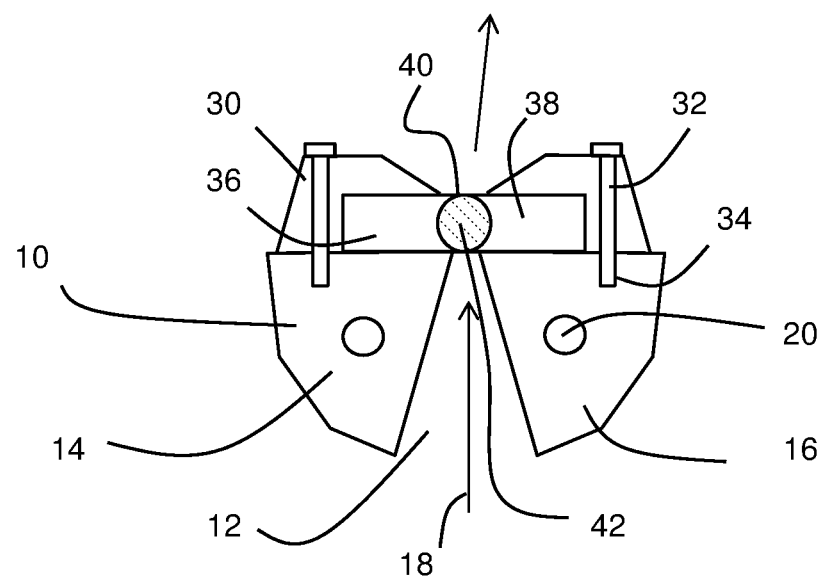
FIG. 2 is a section through the sample holder of FIG. 1 along A-A.
Figure 3:
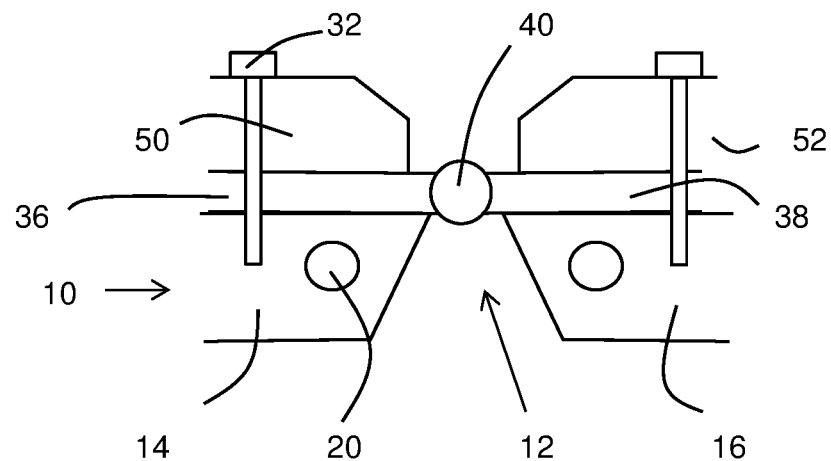
FIG. 3 is a section through an alternative sample holder.

Referring to FIG. 1 (top view) and FIG. 2 (section) a sample holder 2 has a mounting end 4 and an operation end 6. The mounting end 4 is arranged to be fixedly mounted in X-ray diffraction (XRD) apparatus (not shown) and includes mounting holes 8 adapted to the mount in the XRD apparatus. The skilled person will appreciate that different types of XRD apparatus will have different mounts and that the sample holder 2 may be adapted accordingly.

The operation end 6 of the sample holder 2 has a base portion 10 having an opening in the form of a longitudinal slit 12 dividing the base portion 10 into two longitudinally extending base portion parts 14, 16 laterally spaced by the longitudinal slit 12. This provides an X-ray path 18 transversely through the longitudinal slit 12 as illustrated schematically by the arrow. The base portion 10 may be made, for example, of metal such as brass. As may be seen in FIG. 1, the longitudinal split does not extend for the whole length of the operational end, but only in a central region.

Each of the base portion parts 14, 16 may have a duct 20 likewise extending longitudinally for carrying a thermal fluid. The thermal fluid may be replaced by thermal gas. The duct 20 communicates with fluid ports 22 on the mounting end 4 for connection to a thermal regulation system 24. The duct 20 thus forms part of a circulating system by which thermal fluid circulates from one of the fluid ports 22 through the duct 20 in one of the base portion parts 14 towards the operational end 6 and then returns through the duct 20 in the other of the base portion parts 16 to the other fluid port 22 and back to the thermal regulation system 24.

A compression element in the form of a frame 30 is provided which is fixed to base portion 10 by screws 32 engaging with screw holes 34 in base portion 10. Two thermal transport members 36, 38 in the form of pads are held in place by the frame 30. A first thermal transport member 36 is provided on base portion part 14 and a second thermal transport member 38 is provided on the other base portion part 16. The screws 32 act to urge the frame 30 transversely (vertically in FIG. 2) to compress the thermal transport members 36, 38 transversely.

In use, a hollow tube in the form of capillary 40 may be provided. The capillary 40 is mounted above the base portion 10 of the sample holder 2 between the thermal transport members 36, 38. The frame 30 is then mounted on the top and the screws 32 tightened to compress the thermal transport members 36, 38 transversely using the frame 30. Since the thermal transport members 36, 38 have a bulk modulus this causes the side edges of the thermal transport members 36, 38 around capillary 40 to be urged laterally together. This causes the material of the thermal transport members 36, 38 to laterally press against the sides of the capillary 40, in contact with the capillary 40 over the length of the longitudinal slit 12 as well as over a significant part of the capillary 40. In other words, the thermal transport members 36, 38 (as a pair) are not simply in contact with one or two single points around the circumference of the capillary 40 but together cover a significant fraction of the circumference, for example at least 10% but preferably more, for example 20%, 30% or even more preferably 50%.

A sample 42 is contained in the capillary 40. The capillary 40 may be a single shot capillary with a small amount of sample 42 mounted inside the capillary 40 before the capillary 40 is mounted in the sample holder 2.

The temperature is set on thermal regulation system 24 which urges thermal fluid such as water or other thermally conductive liquid through fluid ports 22 and ducts 20 which controls the temperature of the base portion 10. The thermal transport members 36, 38 are in good thermal contact with base portion 10 and with capillary 40 and so the sample 42 is maintained at the desired temperature. The temperature of the fluid is controlled by the thermal regulation system 40 to achieve a desired temperature of the sample 42. To this end, thermometers may be integrated into base portion 10 and a feedback loop maintained.

A beam of X-rays are directed through longitudinal slit 12 onto sample 42 in capillary 40 and are diffracted by a small angle as indicated schematically by the arrow. The small angle of diffraction is measured.

In the embodiment described, the X-rays are used for small angle scattering. The X-rays are provided in the form of a line beam of X-rays travelling in the transverse direction along X-ray path 18, the line beam extending in the longitudinal direction to match the opening in the form of the longitudinal slit 12. Where the sample holder 2 is for holding a sample 42 with X-ray beams of different format, for example an X-ray beam in the form of a circular or square cross section, the shape of the opening can be adapted to match the shape of the intended beam.

Any suitable material may be adopted for thermal transport members 36, 38. In the specific embodiment described, the material used is a pyrolytic highly oriented graphite sheet, which is commercially available and which has a high thermal conductivity. Alternative materials are available—thermally conductive rubber or plastics may be used, as may be polymer loaded with conductive material. Alternatively, graphite or gallium may be used. The material used in this embodiment is softer than the materials used for frame 30 and base 10 as well as having good thermal conductive properties. The thermal transport members 36, 38 may be formed of a single closed loop, i.e. may both be part of a single body.

In the example shown above, the compression element 30 is a single frame. In an alternative example shown in FIG. 3, two separate frame elements, a first frame element 50, and a second frame element 52, have the same function. Each may independently be urged transversely by screws 32 to transversely compress the thermal transport members 36,38 between the frame elements and hence to urge the thermal transport members 36,38 against the hollow tube 40 to both hold the hollow tube and to provide a good thermal path to the hollow tube.

Note that in this example, the diameter of the hollow tube 40 is less than the gap between the thermal transport members 36, 38 when the thermal transport members 36, 38 are not compressed. Accordingly, the hollow tube can easily be inserted and removed since it is only held after the screws 32 are tightened.

Figure 4:
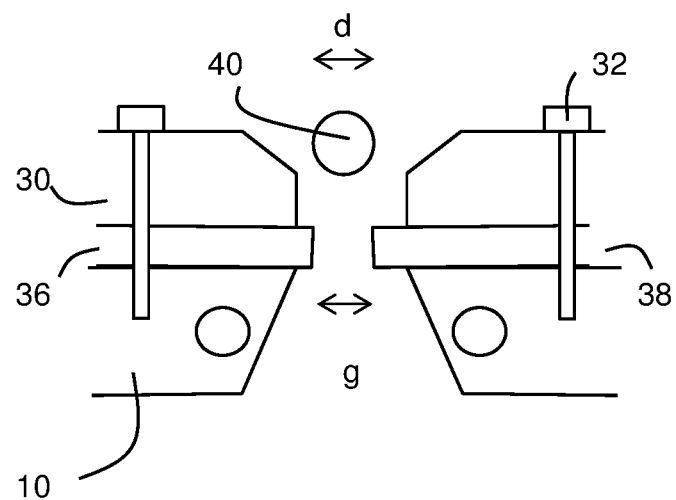
FIG. 4 is a section through a further alternative sample holder.

In an alternative embodiment, illustrated in FIG. 4, with a single frame 30, shown in a state with the hollow tube 40 not mounted, the diameter d of the hollow tube is greater than the gap g between the first and second thermal transport members 36,38 even with the screws 32 untightened and no transverse pressure being exerted on the thermal transport members 36, 38. In this case, the tube 40 can be mounted and held between the thermal transport members 36,38 without tightening the screws 32. The screws 32 only serve to hold the thermal transport members 36,38 between the frame 30 and the base 10 to enable the sample holder to be disassembled, for example for cleaning.

By not requiring the screws to be tightened and untightened when mounting or dismounting the sample holder, the arrangement of FIG. 4 can speed up a sample change.

The thermal transport members 36,38 are in this example made of an elastic material, i.e. a material with sufficient resilience that they can spring back into their original shape with gap g between them when the hollow tube 40 is removed.

Figure 5:
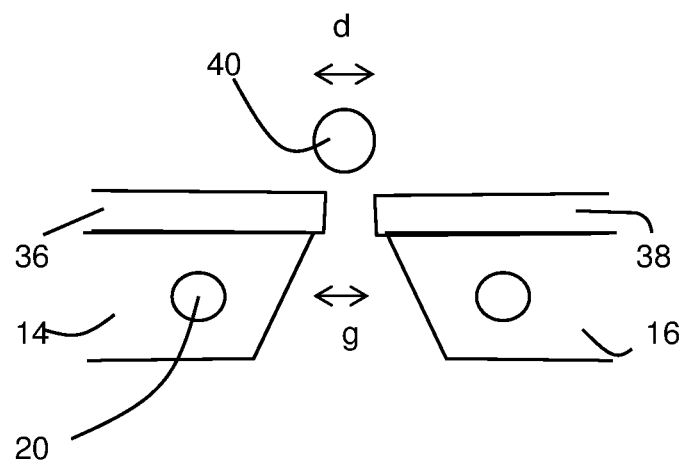
FIG. 5 is a section though a further alternative sample holder.

In a further embodiment, illustrated in FIG. 5, the frame 30 is omitted and the thermal transport members 36,38 are glued to the base portion parts 14,16 again with the gap g between the thermal transport members 36,38 less than the diameter of the hollow tube 40.

This provides a simple structure.

Note that the use of glue to mount the thermal transport members 36,38 to the base portion parts 14,16 may also be used in the examples above.

Figure 6:
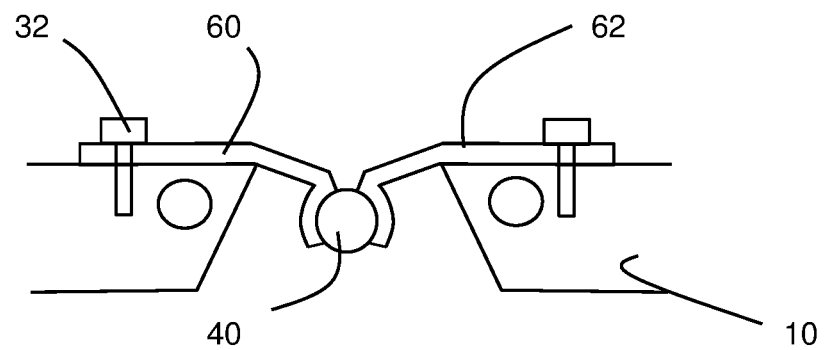
FIG. 6 is a section through a yet further alternative sample holder.
Figure 7:
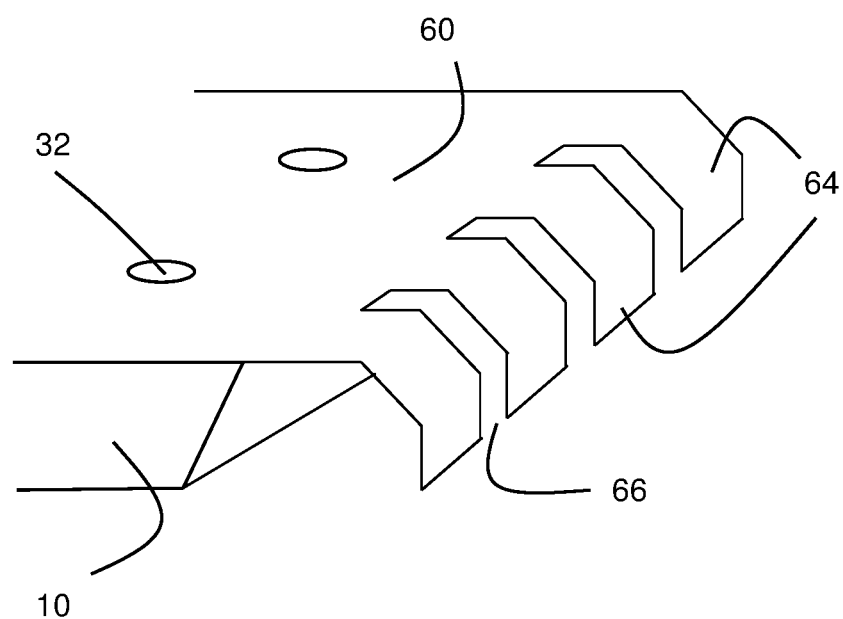
FIG. 7 is a perspective view of the sample holder of FIG. 6.
Figure 8:
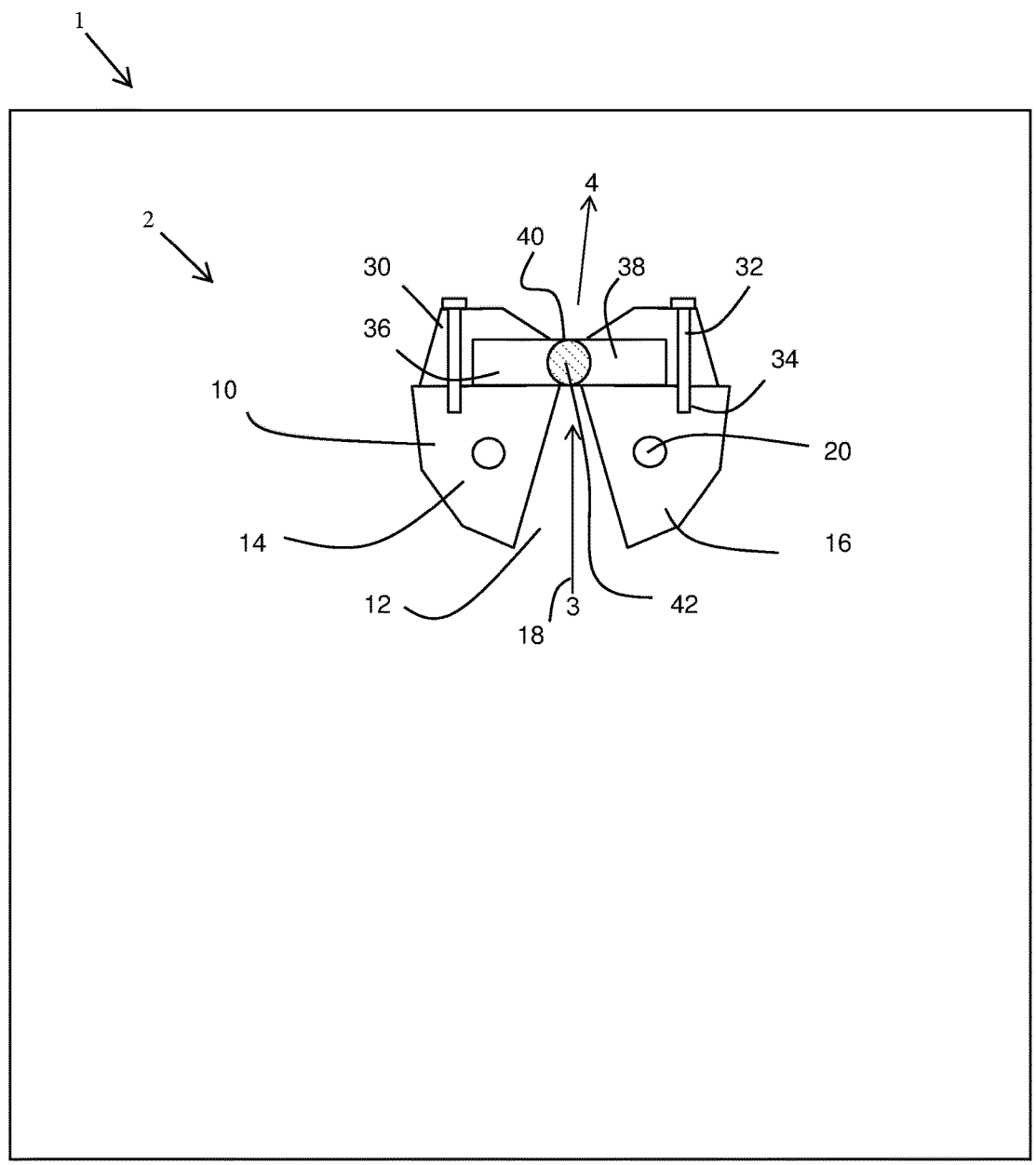
FIG. 8 shows an X-ray apparatus (1) containing the sample holder (2), the X-ray source (3) and the X-ray detector (4).

In a yet further example, illustrated in FIGS. 6 and 7, the thermal transport members are shaped spring elements 60,62 held on to the base portion parts 14,16 by screws 32 to ensure good thermal contact to the base portion parts 14,16. The shaped spring elements 60,62 have elastic fingers 64 on their ends separated by notches 66 in the spring elements 60,62. Note that the shaping of the spring elements matches the shape of the intended hollow tube—i.e. the elastic fingers 64 are curved, to achieve good thermal contact to the tube over an extended area not merely a point.

The size of the hollow tube or capillary may be varied depending on the sample. Indeed, it will be noted that the approach used does not require a capillary of a particular exact size. Different size frames 30 and thermal transport members 36 may allow for a wide variety of sizes of hollow tube.

The hollow tube may be quartz or glass or any other material capable of holding a sample without interfering too much in the X-ray measurements.

The thermal regulation system 24 may be used for heating or cooling as required.

Instead of the cooling arrangements with ducts 20 as described above the base portion 10 may include a Peltier cell, heat-pipe or similar in order to transport heat from or to the base portion.

Those skilled in the art will realise that the above embodiments are by way of example only and that features described with reference to one embodiment may also be applied to other embodiments.

The invention claimed is:

1. A sample holder for holding a hollow tube for X-ray analysis apparatus, comprising:
   a base portion having an opening for an X-ray beam;
   a first thermal transport member on the base portion on one lateral side of the opening and a second thermal transport member on the other lateral side of the opening;
   wherein the first thermal transport member and the second thermal transport member are deformable to compress the hollow tube laterally to hold the hollow tube such that:
   (i) an X-ray beam can pass through the hollow tube without intersecting any part of the sample holder, and
   (ii) there is thermal contact between the hollow tube and the first thermal transport member and the second thermal transport member along the length of the hollow tube and around at least part of the circumference of the hollow tube to conduct heat between the hollow tube and the base portion through the first thermal transport member and the second thermal transport member.

2. A sample holder according to claim 1, further comprising a compression element for compressing the first thermal transport member and/or the second thermal transport member to urge the first thermal transport member and the second thermal transport member together to hold the hollow tube.

3. A sample holder according to claim 2, wherein the compression element is arranged to compress the first thermal transport member and the second thermal transport member between the compression element and the base portion in the transverse direction to urge edges of the first thermal transport member and the second thermal transport member together, to hold the hollow tube extending in a longitudinal direction along the opening.

4. A sample holder according to claim 2, wherein the first thermal transport member and the second thermal transport member are softer than the base portion and softer than the compression element.

5. A sample holder according to claim 4, wherein the first thermal transport member and the second thermal transport member are elastic.

6. A sample holder according to claim 2, further comprising a plurality of screws passing at least partially through the compression element and through the base portion.

7. A sample holder according to claim 1, wherein the opening is a longitudinal slit.

8. A sample holder according to claim 1, further comprising channels in the base portion for containing cooling or heating fluid.

9. A sample holder according to claim 1, further comprising a Peltier cell or heat pipe integrated with the base portion.

10. A sample holder according to claim 1, wherein the first thermal transport member and the second thermal transport member are fixed to the base portion.

11. A sample holder according to claim 1, wherein the first thermal transport member and the second thermal transport member are of graphite or graphenic carbon.

12. A sample holder according to claim 1, wherein the first thermal transport member and the second thermal transport member are of aluminium, gallium, indium or an alloy thereof.

13. A sample holder according to any claim 1, wherein the first thermal transport member and the second thermal transport member are in the form of a metal spring.

14. An X-ray apparatus for small angle X-ray scattering comprising:
   a hollow tube for X-ray analysis apparatus;
   a sample holder comprising:
      a base portion having an opening for an X-ray beam; and
      a first thermal transport member on the base portion on one lateral side of the opening and a second thermal transport member on the other lateral side of the opening;
   an X-ray source for supplying an X-ray beam through the opening to a sample mounted in the hollow tube; and
   an X-ray detector arranged to detect X-rays scattered by the sample;
   wherein the first thermal transport member and the second thermal transport member are deformable to compress the hollow tube laterally to hold the hollow tube such that:
      (i) an X-ray beam can pass through the hollow tube without intersecting any part of the sample holder, and
      (ii) there is thermal contact between the hollow tube and the first thermal transport member and the second thermal transport member along the length of the hollow tube and around at least part of the circumference of the hollow tube to conduct heat between the hollow tube and the base portion through the first thermal transport member and the second thermal transport member.

15. An X-ray apparatus according to claim 14, wherein the X-ray detector is arranged to detect X-rays scattered by the sample by a small angle less than 8°.

16. An X-ray apparatus according to claim 14, wherein the sample holder further comprises a compression element for compressing the first thermal transport member and/or the second thermal transport member to urge the first thermal transport member and the second thermal transport member together to hold the hollow tube.

17. An X-ray apparatus according to claim 16, wherein the compression element is arranged to compress the thermal transport members between the compression element and the base portion in the transverse direction to urge edges of the first thermal transport member and the second thermal transport member together, to hold the hollow tube extending in a longitudinal direction along the opening.

18. An X-ray apparatus according to claim 14, wherein the hollow tube is a glass capillary or a quartz capillary.

* * * * *